United States Patent [19]

Park

[11] Patent Number: 4,771,493
[45] Date of Patent: Sep. 20, 1988

[54] ADJUSTABLE THERAPEUTIC PILLOW

[76] Inventor: Dong-Rae Park, 3721 Cabana La., Plano, Tex. 75023

[21] Appl. No.: 54,025

[22] Filed: May 26, 1987

[51] Int. Cl.⁴ .............................................. A47G 9/00
[52] U.S. Cl. ........................................ 5/437; 5/440; 269/328
[58] Field of Search .................. 5/434, 436, 437, 440, 5/446, 465; 128/133, 134; 269/328

[56] References Cited

U.S. PATENT DOCUMENTS

| | | | |
|---|---|---|---|
| 2,492,383 | 12/1949 | Jones | 5/437 |
| 2,556,629 | 6/1951 | O'Brien | 5/437 |
| 2,902,993 | 9/1959 | Wagner | 5/436 |
| 3,347,544 | 10/1967 | Uffenorde | 269/328 |
| 3,650,523 | 3/1972 | Darby, Jr. | 128/134 |
| 3,737,923 | 6/1973 | Prolo | 128/134 |
| 4,017,118 | 4/1977 | Cawley | 5/440 |
| 4,045,678 | 8/1977 | Rickard | 269/328 |
| 4,182,322 | 1/1980 | Miller | 128/133 |
| 4,285,081 | 8/1981 | Price | 5/434 |
| 4,321,718 | 3/1982 | Chern | 5/437 |
| 4,447,922 | 5/1984 | Brochu | 5/434 |
| 4,535,878 | 8/1985 | Grahl | 190/1 |
| 4,545,572 | 10/1985 | Day | 269/328 |
| 4,571,757 | 2/1986 | Zolecki | 5/437 |
| 4,617,691 | 12/1986 | Monti et al. | 5/434 |

Primary Examiner—Alexander Grosz
Assistant Examiner—Eric K. Nicholson
Attorney, Agent, or Firm—Dennis T. Griggs

[57] ABSTRACT

Adjustable therapeutic pillow apparatus is provided for applying a gentle traction force to the head, neck and shoulders region of a user. The apparatus includes a base, first and second pillow members having spaced-apart convex pillow surfaces for engagement with the user, and means for fastening the pillow members to the base. The apparatus is adjustable in that both the lateral spacing of the pillow members and the overall length of the pillow members may be adjusted.

5 Claims, 4 Drawing Sheets

ADJUSTABLE THERAPEUTIC PILLOW

FIELD OF THE INVENTION

The present invention relates to pillows for the support the head and neck of a patient for therapeutic treatment, and more particularly to a therapeutic pillow apparatus which is adjustable for proper alignment and support.

BACKGROUND OF THE INVENTION

Pillows are generally used to provide a comfortable reclining support for a user's head. While most pillows are designed for purely aesthetic and comfort-related purposes, certain pillows have been used for a combination of utilitarian and therapeutic purposes. For example, U.S. Pat. No. 4,535,878 discloses a pillow-tote bag device having a bifurcated pillow structure for the comfort of a user when lying in either a supine or prone position. In contrast, U.S. Pat. No. 4,330,892 discloses a pillow structure wherein integral magnets are provided to stimulate blood circulation of the user by means of magnetic action. U.S. Pat. No. 2,556,629 discloses a bifurcated pillow construction for the user in a face-down prone position having angularly adjustable frames for the pillow sections. U.S. Pat. Nos. 4,447,992, 3,347,544 and 4,285,081 disclose unitary pillow apparatus having a generally upwardly concave shape with respect to the user's head and neck. U.S. Pat. No. 4,617,691 discloses a multi-piece therapeutic pillow having pillow segments of various sizes joined together by fastening means around the neck of the user. U.S. Pat. No. 3,347,544 discloses a generally concave upwardly pillow apparatus for use as a headrest during eye surgery.

SUMMARY OF THE INVENTION

The present invention includes an adjustable therapeutic pillow apparatus intended for cradling the neck of the user and applying gentle traction force to the neck. The apparatus includes a pair of opposed pillow members separated by a gap and having smooth convex surfaces. The apparatus is adjustable in that the length of the pillow members may be varied as well as the lateral spacing between the pillow members.

BRIEF DESCRIPTION OF THE DRAWINGS

A more complete understanding of the invention and its advantages will be apparent from the Detailed Description taken in conjunction with the accompanying drawings in which.

DETAILED DESCRIPTION OF THE PREFERRED EMBODIMENT

Figure 1:
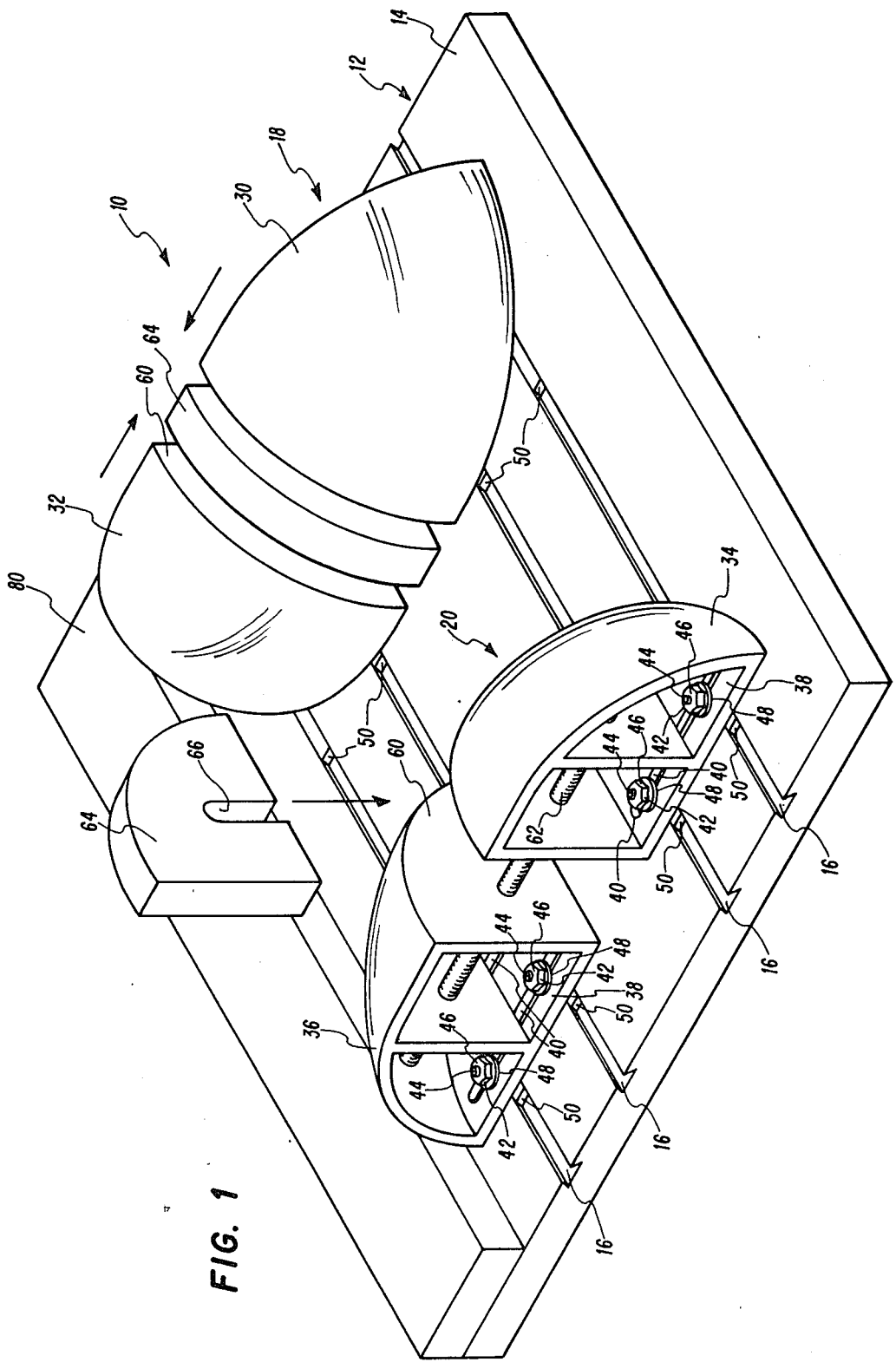
FIG. 1 is a partially exploded perspective view of the invention.
Figure 2:
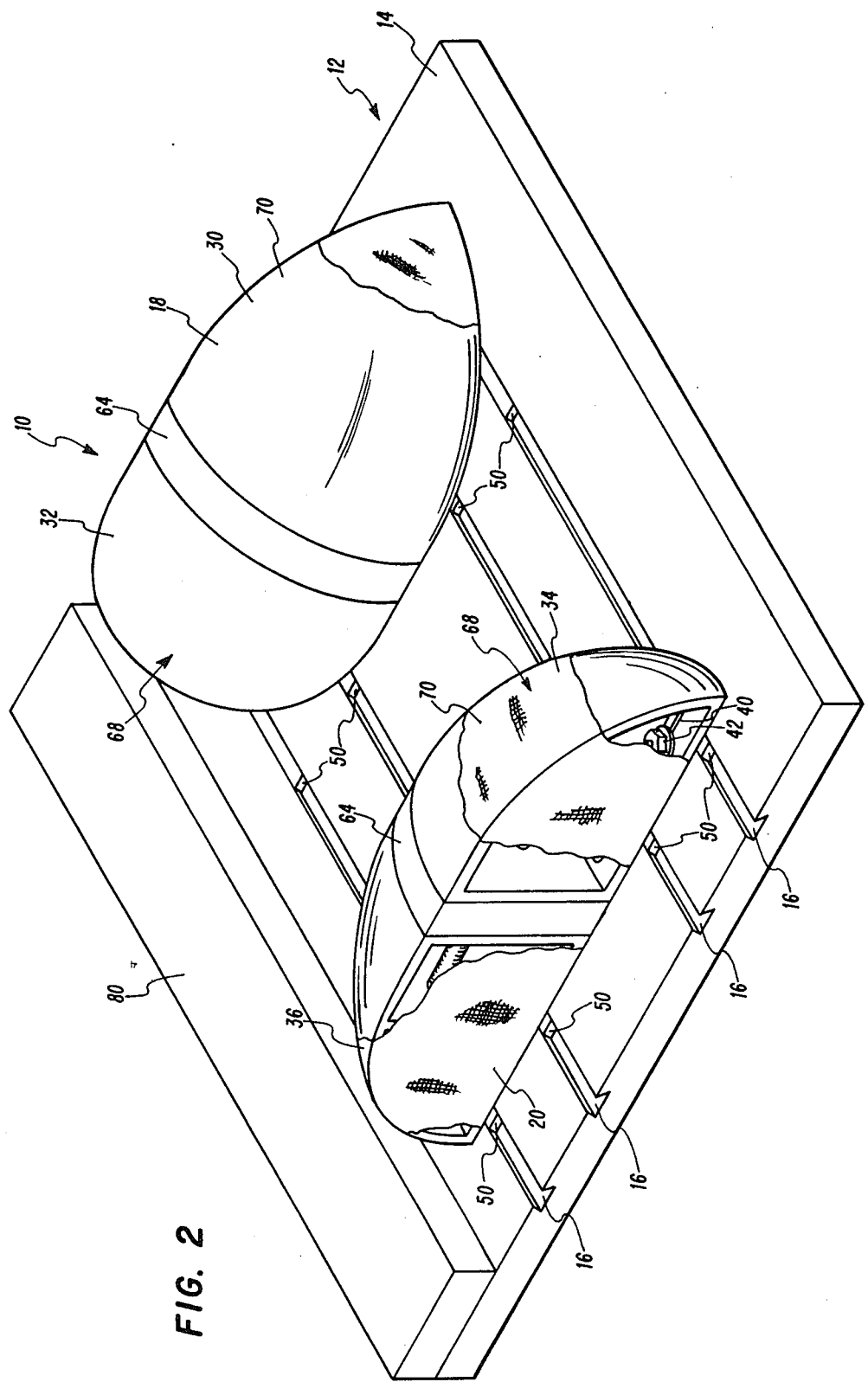
FIG. 2 is a perspective view of the invention in assembled form and having cloth coverings over the pillow elements.
Figure 3:
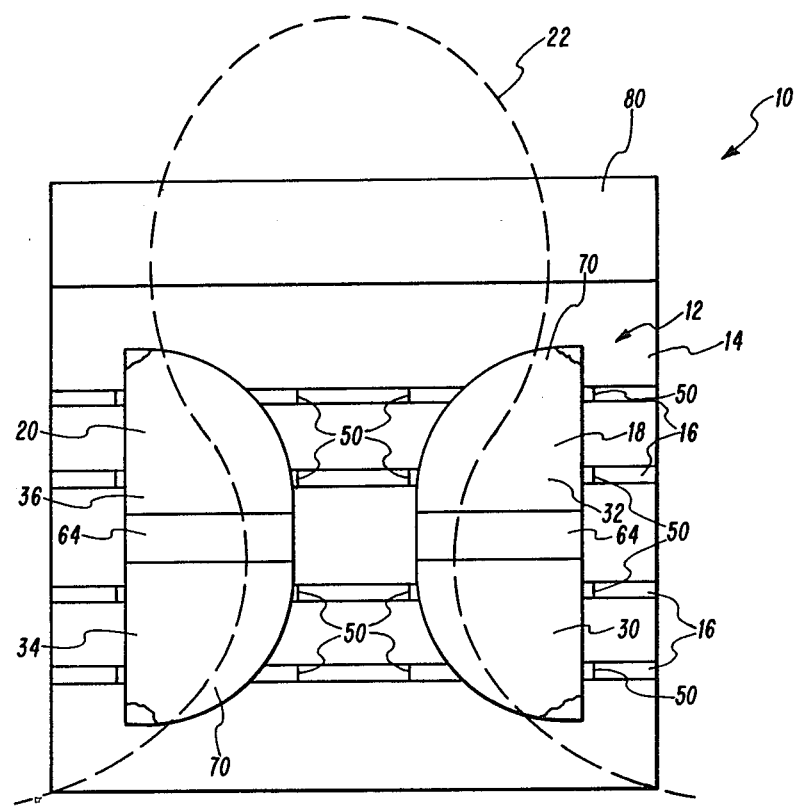
FIG. 3 is a plan view of the invention.
Figure 4:
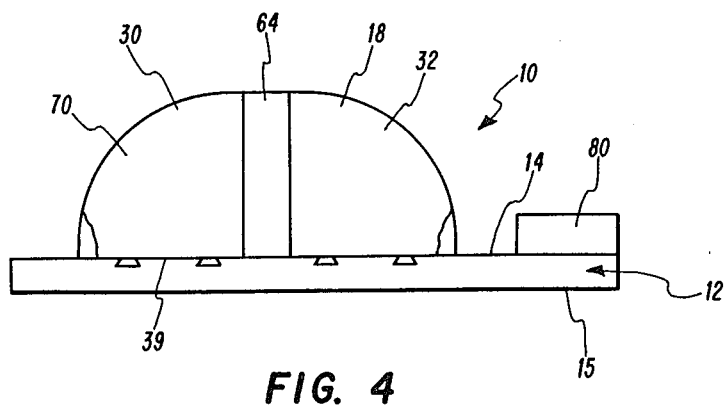
FIG. 4 is a side elevation view of the invention.
Figure 5:
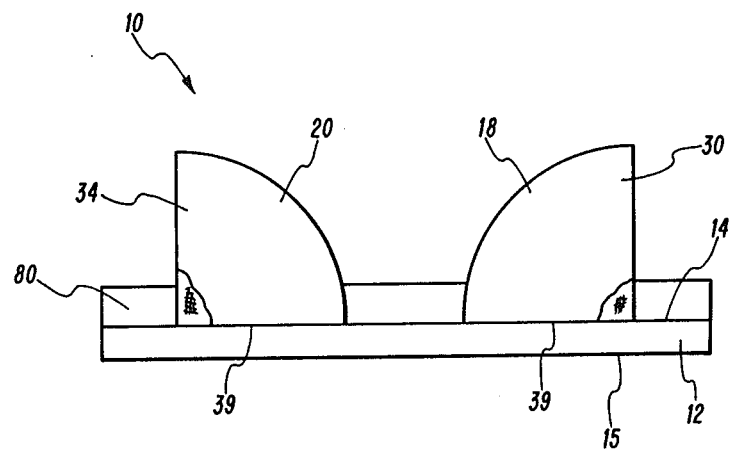
FIG. 5 is a front elevation view of the invention.

Referring initially to FIGS. 1-5, apparatus 10 includes a base 12 having a horizontal planar upper surface 14 and a horizontal planar lower surface 15. Base 15 includes a number of dovetail mortise slots 16 running transversely across base 12 and inset in upper surface 14. Apparatus 10 includes a pair of transversely spaced-apart elongated pillow members 18 and 20. In use, each pillow member 18 and 20 is fixed to base 12, but the transverse space between them is adjustable prior to use to accommodate the head, neck and shoulders portion of patient 22, as shown in FIG. 3.

Pillow member 18 includes a first pillow member element 30 and a second pillow member element 32, and pillow member 20 includes a first pillow member element 34 and a second pillow member element 36. Each of the pillow member elements has a lower wall 38 having a lower planar surface 39 in contact with upper surface 14 of base 12. Each lower wall 38 includes a plurality of longitudinal slots 40 through which fasteners 42 extend. In preferred form, fasteners 42 include threaded studs 44 to which nuts 46 and washers 48 are connected. Washers 48 are sized more largely than slots 40. Threaded studes 44 extend through slots 40 to tenon members 50. Each tenon member 50 has a trapezoidal cross section such that it may be slidably interfitted within a mortise slot 16. The threaded studs 44 are fixed to tenon members 50, such that when nuts 46 are tightened, the tenon members are drawn upwardly within the mortise slots to lock the pillow member element to the base when the desired transverse spacing is obtained.

The length of each pillow member 18 and 20 is also adjustable. As best shown in FIG. 1, each pillow member element includes a vertical transverse wall 60, with the vertical transverse wall 60 of each pillow member element being separated by a gap from and in a parallel plane with the vertical transverse wall 60 of the other pillow member element of that pillow member. A threaded rod 62 extends between the first and second pillow member elements through registered threaded holes in the vertical transverse walls 60. Each threaded rod 62 includes opposite handed threads on the two ends thereof, such that rotation of the rod in one direction causes the first and second pillow member elements to be longitudinally translated towards each other to narrow the gap between the transverse walls 60, and rotation of the rod 62 in the opposite direction causes the pillow member elements to be longitudinally translated away from each other. When nuts 46 are loosened, the pillow member elements are free to move with respect to each other in a longitudinal direction, with the threaded studs 44 being movable within longitudinal slots 40. A spacer block 64 is provided to fill the gap between the transverse walls 60. Spacer block 64 includes a notch 66 for engagement with rod 62. Multiple spacer blocks 64, of varying widths, may be provided to enhance the adjustability of the apparatus.

Each first pillow member element, second pillow member element and spacer block has a convex surface. The pillow surfaces are matched, such that each pillow member includes a smooth pillow member surface 68 (FIG. 2) opposite the pillow member surface 68 of the other pillow member for engagement with the head, neck and shoulders of the user. The pillow surfaces of the pillow members 18 and 20 may optionally be covered with a cloth covering 70, as best shown in FIG. 2, which may be a separate covering for each pillow member element and spacer block as shown in the figures. The pillow member surfaces 68 are formed of a rigid, hard material, such as plastic or fiberglass, and a head block 80 is provided at one end of base 12 transversely spanning base 12. Each pillow member element has an open longitudinal side, as shown in FIG. 1, for access to the threaded rods 62 and fasteners 42 when cloth coverings 70 are removed.

Figure 6:
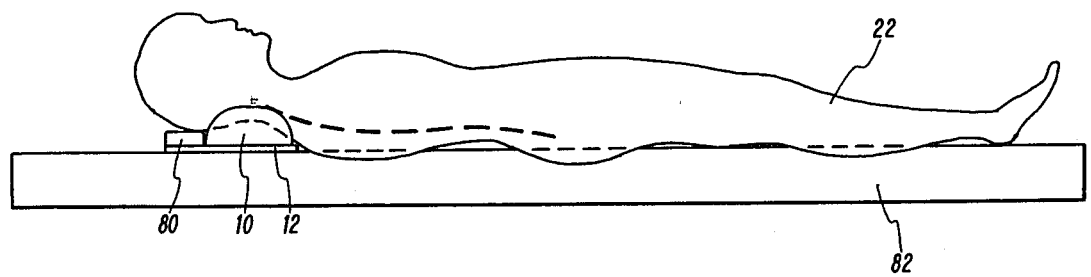
FIG. 6 is a side view of the invention in use.

In operation, as shown in FIG. 6, the apparatus of the present invention engages user 22 in the head, neck and shoulders region. The convex pillow member surfaces provide a gentle traction force to the neck to correct a misaligned cervical spine and to reduce neck and shoulder pain. The user's head rests on block 80, and the user's body rests upon a mattress pad 82. The adjustability of the apparatus in both length of the pillow members and lateral spacing of the pillow members allows the apparatus to be adapted for optimum use for persons of different sizes.

Various combinations of spacer blocks provide both narrow and wide firm borders for neck support. When lying on the back, the user's head and neck can be neutral, forward flexed, or in normal extension. The pillow helps to mobilize soft tissue, open neural foramina to relieve cervical nerve root pressure, improve the body's muscle balance and posture, and restore normal cervical curvature.

While a preferred embodiment of the apparatus according to the invention has been described and shown in the drawings, any modifications thereof may be made by persons skilled in the art without departing from the spirit of the invention, and it is intended to project by Letters Patent all forms of the invention falling within the scope of the following claims.

What is claimed is:

1. Adjustable therapeutic pillow apparatus comprising:
   a base;
   a first pillow member having a convex surface;
   a second pillow member having a convex surface opposite and spaced apart from the convex surface of the first pillow member;
   said first and second pillow members each including first and second pillow member elements separated by a gap, the width of the gap being adjustable to adjust the length of the pillow member; and,
   means for fastening the first and second pillow members to the base, the means being adjustable to permit variations in the distance the pillow members are spaced apart when fastened to the base.

2. The apparatus of claim 1 further comprising a spacer block located in each gap between pillow member elements, such that the convex surface of the pillow member is smooth.

3. The apparatus of claim 1 wherein each pillow member element includes a longitudinal slot in which the means for fastening is restrained for permitting adjustment of the gap between the pillow member elements.

4. The apparatus of claim 3 wherein a threaded member extends through the slot of each pillow member element for fixing the gap between the pillow member elements.

5. An adjustable pillow apparatus, comprising:
   a base having a horizontal planar upper surface and a horizontal planar lower surface;
   walls defining a plurlaity of transverse dovetail mortise slots in the upper surface of the base;
   a pair of transversely spaced-apart elongated pillow members, each pillow member being comprised of first and second pillow member elements;
   the first and second pillow member elements each having a lower planar surface in contact with the upper surface of the base;
   the lower surfaces of the pillow elements further including walls defining a plurality of longitudinal slots in the lower surfaces;
   a plurality of tightenable fasteners extending through and confined by the longitudinal slots of the pillow member elements;
   the fasteners being attached to tenon members slidably engaged in the mortise slots of the base upper surface, such that the first and second pillow member elements of each pillow member may be slidably translated in a transverse direction by sliding movements of the tenon members in the mortise slots and slidably translated in a longitudinal direction by movement of the fasteners in the longitudinal slots of the pillow member elements, with the pillow member elements being fixable with respect to the base by the tightening of the fasteners;
   each first and second pillow member element including at least one vertical transverse wall, the vertical transverse wall of each first pillow member element of a pillow member being separated by a gap from and in a parallel plane with the vertical transverse wall of the second pillow member element of that pillow member;
   a threaded rod extending between the first and second pillow member elements of each pillow member through registered threaded holes in the vertical transverse walls of the pillow member elements, each threaded rod including opposite handed threads on the two ends thereof such that rotation of the rod in one direction causes the first and second pillow member elements to be longitudinally translated towards each other to narrow the gap between the pillow member elements and rotation of the rod in the opposite direction causes the pillow member elements to be longitudinally translated away from each other;
   each first and second pillow member element further including an open longitudinal side for access to the threaded rod and the fasteners;
   at least one spacer block filling each gap between first and second pillow member element vertical transverse walls; and
   each first pillow member element, second pillow member element and spacer block having matched convex pillow surface segments such that each pillow member includes a smooth pillow member surface opposite the pillow member surface of the other pillow member.

* * * * *

UNITED STATES PATENT AND TRADEMARK OFFICE
CERTIFICATE OF CORRECTION

PATENT NO. : 4,771,493

DATED : September 20, 1988

INVENTOR(S) : Dong-Rae Park

It is certified that error appears in the above-identified patent and that said Letters Patent is hereby corrected as shown below:

Column 1, line 67, "15" should be -- 12 --.

Column 2, line 18, "studes" should be -- studs --.

Column 4, line 3, "plurlaity" should be -- plurality --.

Signed and Sealed this

Twenty-fourth Day of January, 1989

Attest:

DONALD J. QUIGG

*Attesting Officer*     *Commissioner of Patents and Trademarks*